US009571146B2

(12) United States Patent
Penafiel

(10) Patent No.: US 9,571,146 B2
(45) Date of Patent: Feb. 14, 2017

(54) DETECTION AND ASSESSMENT OF RADIO FREQUENCY EMISSIONS

(71) Applicant: Trust Battery Ireland Limited, Dublin (IE)

(72) Inventor: Luis Miguel Penafiel, Kensington, MD (US)

(73) Assignee: TRUST TECHNOLOGY WORLD DMCC, Dubai (AE)

( * ) Notice: Subject to any disclaimer, the term of this patent is extended or adjusted under 35 U.S.C. 154(b) by 0 days.

(21) Appl. No.: 14/823,498

(22) Filed: Aug. 11, 2015

(65) Prior Publication Data

US 2015/0349829 A1 Dec. 3, 2015

Related U.S. Application Data

(63) Continuation of application No. 13/876,882, filed as application No. PCT/EP2011/004892 on Sep. 30, 2011, now Pat. No. 9,124,349.

(30) Foreign Application Priority Data

Oct. 1, 2010 (IE) .................................... 2010/0660

(51) Int. Cl.
*H04M 1/00* (2006.01)
*H04B 1/3827* (2015.01)
(Continued)

(52) U.S. Cl.
CPC .............. *H04B 1/3838* (2013.01); *A61N 1/16* (2013.01); *H04M 1/0202* (2013.01); *H04W 24/08* (2013.01); *H04M 1/21* (2013.01)

(58) Field of Classification Search
CPC ........................... H04B 1/3838; H04B 1/0202
(Continued)

(56) References Cited

U.S. PATENT DOCUMENTS 5,544,665 A  8/1996 Litovitz et al.
5,566,685 A  10/1996 Litovitz et al.
(Continued)

FOREIGN PATENT DOCUMENTS

GB      2484167 A      4/2012
IE      2010/0660 A1   4/2012
(Continued)

OTHER PUBLICATIONS

Corresponding PCT Application No. PCT/EP2011/004892 filed Sep. 30, 2011; Published as 2012/041514 A1 on Apr. 5, 2012.
(Continued)

*Primary Examiner* — Sonny Trinh
(74) *Attorney, Agent, or Firm* — The Dobrusin Law Firm, P.C.

(57) ABSTRACT

A device adapted to fit within, or to be positioned adjacent to, a cellular handset or other personal communication device, for remedying the potentially harmful effect on humans or animal life of RF transmissions, and including an antenna responsive to the presence of RF radiation generated by the handset, signal analysis means for identifying the type of RF transmissions detected which is coupled to activate remedial signal generation means, which is arranged to provide a noise signal to a coil for providing an electromagnetic field in the vicinity of the handset, to disrupt the potentially harmful effects of the RF transmissions.

18 Claims, 5 Drawing Sheets

(51) Int. Cl.
*H04W 24/08* (2009.01)
*A61N 1/16* (2006.01)
*H04M 1/02* (2006.01)
*H04M 1/21* (2006.01)

(58) Field of Classification Search
USPC .......... 455/575.5, 575.8, 575.1, 575.7, 90.3; 343/702, 841
See application file for complete search history.

(56) References Cited

U.S. PATENT DOCUMENTS

| | | | |
|---|---|---|---|
| 6,564,038 B1 | 5/2003 | Bethea | |
| 6,947,000 B2 | 9/2005 | Ito | |
| 6,957,051 B1 | 10/2005 | Korisch et al. | |
| 6,985,113 B2* | 1/2006 | Nishimura | H01Q 1/245 343/700 MS |
| 7,099,632 B2* | 8/2006 | Hong | H04M 1/0216 343/702 |
| 7,146,139 B2* | 12/2006 | Nevermann | H04B 1/3838 343/702 |
| 7,212,502 B2* | 5/2007 | Freyman | H04M 1/74 370/288 |
| 7,274,953 B2* | 9/2007 | Takagi | H04B 1/3838 455/575.2 |
| 7,330,705 B2* | 2/2008 | Lee | H04B 1/3838 455/115.1 |
| 7,672,698 B2 | 3/2010 | Kang | |
| 8,155,721 B2 | 4/2012 | Shanks et al. | |
| 8,290,550 B2 | 10/2012 | Kodama | |
| 8,604,996 B2 | 12/2013 | Xu et al. | |
| 2005/0153754 A1* | 7/2005 | Shanks | H04B 1/3838 455/575.5 |
| 2008/0014872 A1 | 1/2008 | Tucek et al. | |
| 2008/0091238 A1 | 4/2008 | Colliard | |

FOREIGN PATENT DOCUMENTS

| | | |
|---|---|---|
| JP | 2004298646 | 10/2004 |
| JP | 2009544217 | 12/2009 |
| WO | 9501758 | 1/1995 |
| WO | 2005/112593 A2 | 12/2005 |
| WO | 2012/041514 A1 | 4/2012 |

OTHER PUBLICATIONS

Corresponding IE Application No. IE20100000660 filed Oct. 1, 2010; Published as IE 2010/0660 on Apr. 11, 2012.
Corresponding GB Application No. GB 1112263.7 filed Jul. 18, 2011; Published as GB 2484167 A on Apr. 4, 2012.
International Search Report for for corresponding PCT Application No. PCT/EP2011/004892 filed Sep. 30, 2011; dated Feb. 3, 2012.
International Preliminary Report on Patentability for corresponding PCT Application No. PCT/EP2011/004892 filed Sep. 30, 2011; dated Feb. 4, 2013.
Search Report for corresponding IE Application No. IE20100000660 filed Oct. 1, 2010; dated Dec. 9, 2010.
Search Report for Corresponding GB Application No. GB 1112263.7 filed Jul. 18, 2011; dated Nov. 17, 2011.
Amendment to Search Report for Corresponding GB Application No. GB 1112263.7 filed Jul. 18, 2011; dated Jan. 13, 2012.
United Kingdom Intellectual Property Office Combined Search and Examination Report for Application No. GB1420701.3 dated Mar. 25, 2015.
Litovitz et al., The Role of Coherence Time in the Effect of Microwaves on Ornithine Decarboxylase Activity, Bioelectromagnetics, 1993, 395-403, 14.
Litovitz et al., The Role of Temporal Sensing in Bioelectromagnetic Effects, Bioelectromagnetics, 1997, 388-395, 18.
Decision of Refusal from Japanese Patent Office with Date of Drafting Mar. 15, 2016 for Application No. 2013-530624. (English Translation obtained from USPTO Global Dossier).

* cited by examiner

PASSIVE RF DETECTOR

REMEDIAL SIGNAL CONTROL MODULE

DETECTION AND ASSESSMENT OF RADIO FREQUENCY EMISSIONS

The present invention relates to methods and apparatus for protecting living systems from potentially adverse effects upon them of electric fields, magnetic fields and electromagnetic fields.

There are conflicting views as to the effects of electric fields, magnetic fields and electromagnetic fields on living systems. However there is considerable evidence that certain fields may be damaging to living systems including humans. It may also be that the detrimental effects are long term and their full impact has not yet been realised.

There has been a dramatic increase around the world in the use of electrically operated devices. All such devices have associated with them electromagnetic field emissions which, to varying degrees, have the potential to affect human health. Of particular interest are devices that transmit radio frequency (RF) signals and are used in close proximity to the human body, for instance cellular phones and other personal communication devices. At issue is the possibility that the safety standards under which these devices are manufactured which establish RF exposure limits to the users of these devices may not adequately account for effects below the thermal threshold, that is, at exposure levels well below levels that can produce measurable heating and can be attributed to direct energy transfer. The potential for such low level effects is supported by substantial evidence from epidemiologic studies and laboratory research which suggests that any measures that could minimize the effects of such exposure would be beneficial to the users of these devices U.S. Pat. No. 5,544,665 is concerned with the protection of living systems from the harmful effects of electromagnetic fields and states that certain fields have an effect on the enzyme ornithine decarboxylase. The patent states that the potentially damaging effect can be reduced or eliminated if the detrimental electromagnetic field is altered either by switching the field on and off or superimposing an electromagnetic noise field upon it. The patent further states that the effect can only be reduced if such alteration causes relevant characteristic properties of the field to change in time at intervals of less than 5 seconds and preferably at intervals from 0.1 to 1 second. The characteristic properties that can be changed are said to be frequency, phase, direction, waveform or amplitude. Similar effects are discussed in Bioelectromagnetics 14 395-403 (1993) and Bioelectromagnetics 18 388-395 (1997).

U.S. Pat. No. 5,544,665 further describes various applications of the bio-protection scheme including applications to cellular telephones. The EMX Corporation has promoted batteries for cellular telephones that make use of the technology described in U.S. Pat. No. 5,544,665. When used with a cellular phone, these batteries produce a noise electromagnetic field that is superimposed over the local RF field thereby causing the total field to be irregular and thus not likely to cause biological effects. The noise was generated by a coil forming part of the battery pack. Activation of the noise was accomplished by monitoring the flow of electric current from the battery to the phone and using this as an indirect means to determine when the phone was transmitting RF fields that were likely to produce biological effects. This activation technique worked reasonably well with older phones but proved to be unreliable with newer phones which have applications, such as games and other entertainment applications that demand power from the battery, thereby causing the flow of electric current, and can cause false triggering of the noise and potentially unacceptable reduction in battery life.

The present invention overcomes these problems.

The present invention therefore provides a process, an apparatus and systems for the reduction or elimination of the potentially harmful effect on humans or animal life caused by exposure to electromagnetic fields produced by devices that operate by transmitting RF signals, comprising a device provided with means to reduce or eliminate the potentially harmful effect of the RF signals and further provided with a means to sense and analyze RF fields and determine their ability to produce biological effects, and which activates the means to reduce or eliminate the potentially harmful effect of the measured RF signals on humans or animal life.

The invention may be applied to most electronic devices that operate by transmitting RF signals which could be potentially harmful to human or animal life, but it is particularly useful with personal communication devices, such as cellular telephones, that are used in close proximity to the human body.

Earlier studies have shown that RF radiation can cause potentially harmful effects if it is regular, meaning that it has constant properties, and is continuously applied for periods of over 10 seconds and that the potential harm can be substantially eliminated if the regularity period is reduced to no more than 1 second. The means to eliminate the potential harm in the present invention may superimpose a noise electromagnetic field on the potentially harmful radiation to produce a combined field that is irregular in time, meaning that it does not have constant properties in time, and therefore no longer has the potential to cause harm. Use of the noise field, which is hereinafter referred to as the remedial signal, is preferred as it allows for use of the electronic device without altering the manner in which it operates.

Although not limited to such an application, the invention is particularly useful with battery operated personal communication devices. In the preferred embodiment the potentially harmful effect of the RF radiation is inhibited by a means that generates a remedial signal that is superimposed on the RF signal to provide a combined signal that is irregular and therefore has no bio-effecting consequence. Any suitable means may be used but the means may comprise an inductive coil which is activated to produce the remedial signal field, primarily magnetic in nature, employing power from the battery.

A means which senses and identifies the potentially harmful radiation may be any standard RF sensor, for instance an antenna, with accompanying electronics, which have been suitably configured to identify the particular radiation which is emitted by the electronic device and which is considered to be potentially harmful.

As preferred, the apparatus of the invention may be formed essentially as a single unitary component which is adapted to fit within an existing cellular phone handset, or other personal communication device, with little or no modification to the device. For instance, the component may be incorporated inside the battery pack that provides powers to the handset. The component is an electronic circuit that comprises an RF antenna and is coupled to a coil for generating the remedial signal field. The coil may be formed around the battery of the handset. Where the battery is lithium polymer, the coil may be physically pressed into the battery, so as to minimize the space needed to fit this part. Alternatively the component may be separate from the handset, but adapted to be placed next to the handset while the handset is in use to provide a remedial signal. For example the component may be formed as a card article, of credit card dimensions and shape, with electronics incorporated within the card, and a coil for providing the remedial signal being formed around the edge of the card.

The apparatus of the invention may possess its own source of power, or may rely on the power provided by the battery of the handset.

The invention therefore provides more specifically, a remedial device for association with a personal communication device that emits RF transmissions potentially harmful to humans or animal life, the remedial device including sensor means for sensing the presence of said RF transmissions, signal analysis means for assessing the RF transmissions to determine if they are likely to cause biological effects, and a remedial signal generator means, said signal analysis means being coupled for actuation of said remedial signal generator means, and the remedial signal generation means being arranged to establish a remedial electromagnetic field in the vicinity of the handset.

Said sensor means may be an RF sensor, for instance an antenna, which has been suitably configured to detect the particular radiation which is emitted by the electronic device and which is considered to be potentially harmful. Such sensor as preferred comprises an antenna which is responsive to a carrier wave frequency of the cellular handset that is a microwave frequency in the region of 0.8 to 2 GHz, as detailed below. As an alternative to a separate antenna, the coil for establishing the remedial field may be configured to detect RF transmissions. The advantage of this is the loss of the antenna component, but the accompanying disadvantage is the need to configure the coil for two-way operation, for example with a duplexing system. Whilst other methods of sensing the generation of RF transmissions might in theory be employed, for example sensing large current fluctuations in the apparatus, they would require some disturbance or modification of the apparatus. This would create further difficulty, particularly with cellular phone handsets. Further cellular phone handsets are of many different types, in particular with their antenna being in any part of the handset, or perhaps being constituted by the handset itself.

Said signal analysis means for assessing the sensed radiation may comprise an RF detection stage, for detecting RF transmissions that may contain potentially harmful components, together with a signal analysis means, which signal analysis means is arranged to make an analysis of the detected RF transmissions in order to make a positive determination of whether components present in the transmission signal are potentially harmful components. The RF detection stage is arranged to provide an actuation signal to the signal analysis means. In one embodiment the RF detection stage comprises a passive detection stage, followed by an active detection stage, which comprises said signal analysis means. The passive detection stage is arranged to monitor RF emissions from the handset, and to rectify and integrate an RF transmission signal. One or more delayed versions of the detected signal are compared with the current version, in order to determine whether there is RF radiation of significant duration that is likely to cause biological effects. This is typically the case during speech transmission. In this event, a power control signal is generated. The passive detector stage does not require power for its operation, relying on the strength of the received signal, and therefore may be continuously operative, without any drain on the power source. In order to ensure that the sensed RF signal is of sufficient strength for detection, the coil for establishing the remedial field may in addition be configured to sense the RF transmissions, and to provide an additional signal to the detection means, as described below.

The purpose of the passive detection stage is to wake-up the active detection stage to allow more accurate detection of the RF signal and activation of the other system components. The active detection stage is activated in response to the generation of the power control signal by the passive detection stage and includes circuitry which requires a power source for operation. The use of active components allows for power amplification and more accurate sampling of the antenna signal. Circuit components in the active detector stage may be configured to perform a similar function as the passive detector stage, that is, to compare integrated and averaged versions of the antenna signal, with a threshold value. The active detector stage makes a detection of the antenna signal on successive time intervals and generates a signal that can take on various states to indicate the type of signal detected. The signal detection interval of the active stage should be preferably between 100 ms and 1 s. The output of the active detector is employed to activate a remedial signal generator via a remedial signal control module.

Otherwise said signal analysis means signal makes an accurate and reliable determination of the characteristics of the sensed RF signal, in particular, whether the transmission is voice or data and the likely transmission protocol, for instance, GSM, 3G or other commonly used protocols, and whether the particular type of transmission contains potentially harmful components of any nature.

Said signal analysis means may provide an activation signal to a power control module to enable supply of power to said remedial signal generator means (or selected parts thereof). The remedial control generator means may include a remedial signal control module, which provides a control signal to the power source, and a control signal to a remedial signal generator module, for generating the desired form of remedial signal. The remedial signal control module is responsive to an output from the RF detection stage, and preferably comprises a microcontroller for executing one or more algorithms for controlling the remedial signal generator module. As preferred, the control module waits for a period of about 1 second until it receives a continual output from the detection stages, and then requests the power unit to provide power to the generator module, so that the remedial signal is generated for a period of about 3 seconds. The waiting period of about 1 second is significant in that it represents a minimum period in which the presence of an RF signal may trigger a response in living tissue. Any radiation generated by the handset for a period of less than this minimum period is regarded as not requiring remedial action. The period of 3 seconds is chosen on the grounds of convenience, since with a longer period, a remedial field may be generated when it is not required, and a shorter period may result in excessive switching operations within the circuitry. At the end of the 3 second period, the control module is reset unless or until a continual signal is again present from the RF detection stages.

The remedial signal generator module may include a digital noise generator, for example as described in U.S. Pat. No. 5,544,665, which is coupled through digital to analog conversion means and filter means, for providing an analog form of the remedial signal, to a coil which provides a means for establishing the remedial field in the neighbourhood of the handset.

BRIEF DESCRIPTION OF THE DRAWINGS

Embodiments of the invention will now be described, by way of example only, with reference to the accompanying drawings, wherein.

DESCRIPTION OF THE EMBODIMENTS

Figure 1:
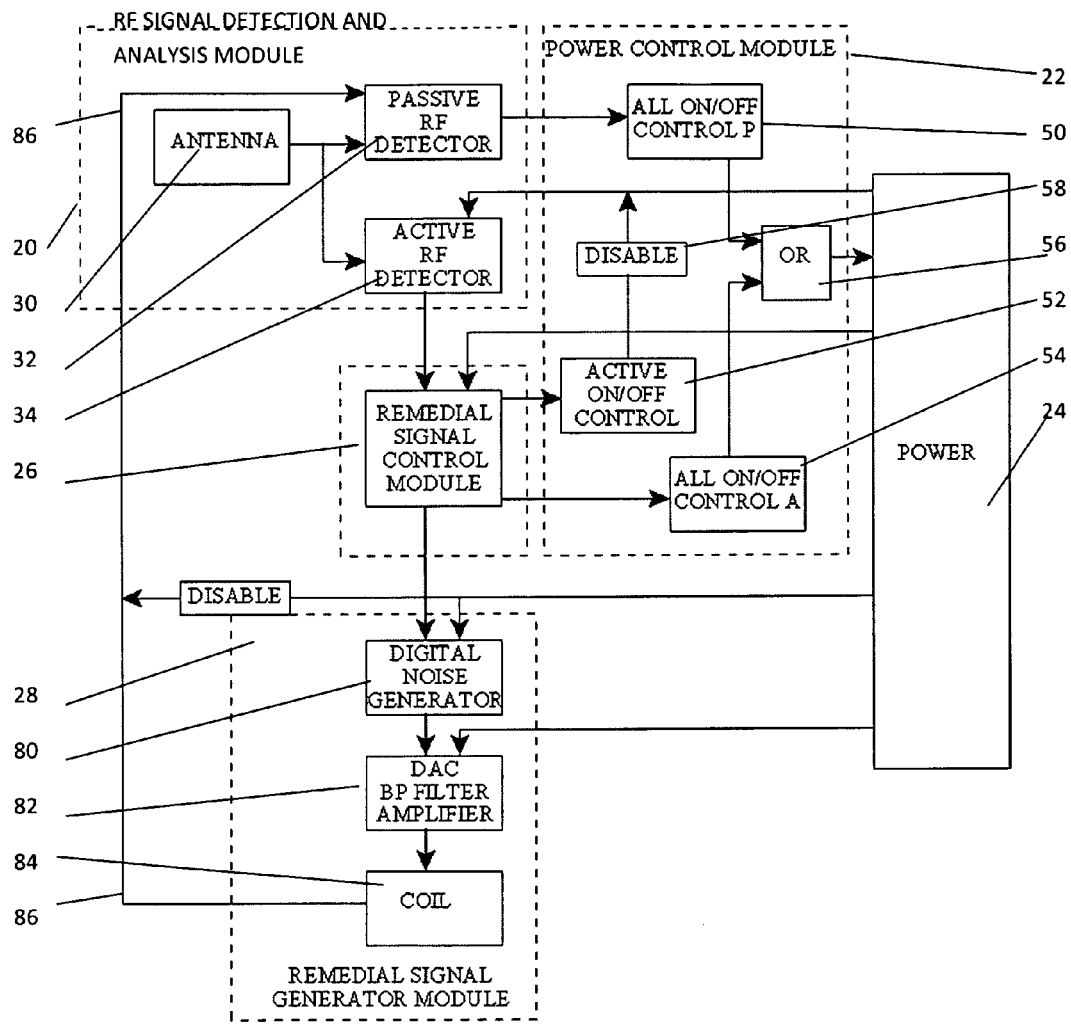
FIG. 1 is a schematic block diagram of the remedial device according to the invention.

All electromagnetic radiation consists of oscillating electric and magnetic fields and the frequency, which is the number of times per second at which the wave oscillates, determines their properties and the use that can be made of them. Frequencies are measured in hertz or Hz, where 1 Hz is one oscillation per second, 1 kHz a thousand, 1 MHz is a million, and GHz, is a thousand million. Frequencies between 30 KHz and 300 GHz are widely used for telecommunications, including broadcast radio and television, and comprise the radio frequency band.

Cellular mobile services operate at frequencies authorised by governments and typically operate within the frequency ranges 872-960 MHz, 1710-1875 MHz and 1920-2170 MHz. These frequencies are within the microwave frequency band which encompasses the range between 300 MHz and 300 GHz. Other applications within this range include radar, telecommunication links, satellite communications, weather observation and medical diathermy. Although this invention may be used with waves of any frequency that are potentially harmful to humans and animal life, it is particularly useful with devices that operate on frequencies used for cellular telephones.

A radio frequency wave used to carry information in radio communications is referred to as a carrier wave. The radio frequency carrier wave of any system is produced by the transmitter as a sine wave, or other regular waveform. A carrier wave conveys no information if its properties do not vary in time. If the carrier wave is to convey any information, for instance, speech, music or digitized data, this information has to be added to it in some way. The process of varying one or more properties of a carrier signal with respect to the information that it is to carry is known as modulation. Properties of the carrier wave that may be varied through modulation include for instance, amplitude, frequency, phase or a combination of these. For example, for AM (amplitude modulation) transmission, the electrical signal from a microphone produced by speech or music is used to vary the amplitude of the carrier wave, so that at any instant the size or amplitude of the RF carrier wave is made proportional to the size of the electrical modulating signal. In FM (frequency modulation), the instantaneous frequency of the carrier deviates from the carrier frequency by an amount dependent on the strength of the modulating signal. Phase modulation (PM) is a form of modulation that represents information as variations in the instantaneous phase of a carrier wave. FM and PM are very commonly used for current day radio communications.

A mobile phone (cell phone) sends and receives information (voice messages, text messages, emails, fax, computer data, downloads information etc) by radio communication. Radio frequency signals are transmitted from the phone to the nearest base station and incoming signals (carrying the information from the source to which the phone user is listening) are sent from the base station to the phone at a slightly different frequency. Base stations link mobile phones to the rest of the mobile and fixed phone network. Once the signal reaches a base station it can be transmitted to the main telephone network, usually by an optical fiber network.

Each base station provides radio coverage to a geographical area known as a cell. Base stations (BS) are connected to one another by a mobile services switching centre (MSC), which tracks calls and transfer them as the caller moves from one cell to the next. An ideal network may be envisaged as consisting of a mesh of hexagonal cells, each with a base station at its centre. The cells overlap at the edges to ensure the mobile phone users always remain within range of the base station. Without sufficient base stations in the right locations, mobile phones will not work. If a person with a mobile phone starts to move out of one cell into another, the controlling network hands over communications to the adjacent base station.

The radiation with which this invention is particularly concerned is that emitted by the cellular telephone when it is transmitting or receiving information and particularly when it is transmitting information and in particular when it is transmitting speech as that is generally the time when it is in closest proximity to the head, and transmission radiation occurs for a significant length of time.

In operation therefore the cellular telephone will be activated for use and will immediately generate the potentially harmful radiation at the particular predetermined frequency. The presence of the radiation will immediately be sensed by the sensor and detection means of the invention, which will then activate the remedial signal (noise) generator means that converts the constant potentially harmful radiation to a random benign wave pattern. The sensor and detection means also detects when the potentially harmful radiation is no longer being generated and deactivates the remedial signal until the next time that it is required. The choice of the frequency of the remedial signal will depend upon the nature of the electrical device and the frequency of the potentially harmful waves it generates. However we have found that for negating the potentially harmful effect of the radiation generated by use of the cellular telephone a remedial signal having a frequency in the range 30 Hz to 90 Hz is particularly useful.

An important aspect of an embodiment is that the radiation sensor and detector and the generator of the remedial signal can be incorporated into the cellular telephone without the need to alter the structure of the cellular telephone itself. We have found that this can be accomplished by the use of a miniaturised printed circuit containing the sensor and the detector and the remedial signal generator incorporated with the battery for the telephone. The invention may be used with any of the battery cells used for cellular telephones such as lithium ion batteries but use with the softer batteries such as lithium polymer batteries may be advantageous since the printed circuit board containing the components of this invention and the coil can be pressed into the battery casing to provide a battery with minimal reduction in battery capacity relative to a standard equivalent battery.

Figure 4:
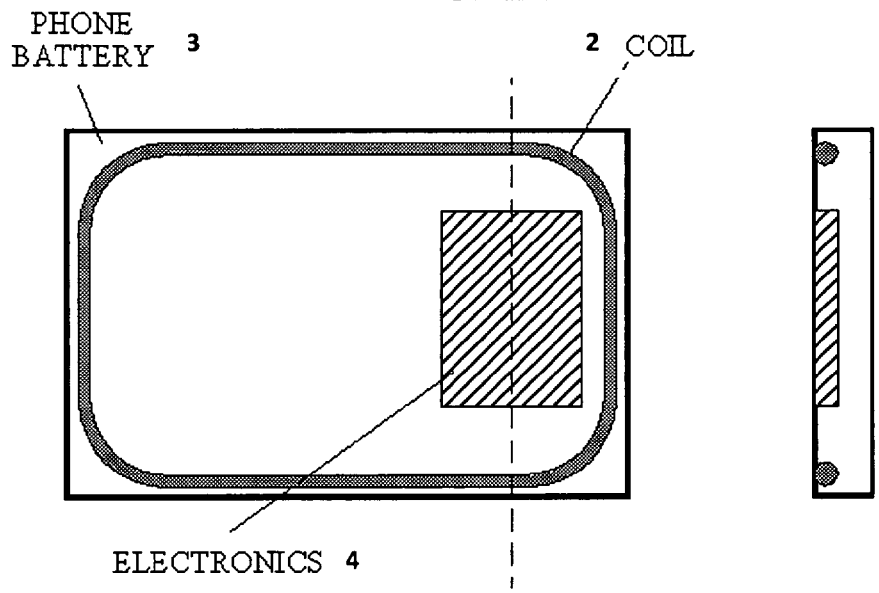
FIG. 4 is a plan view and sectional view of a remedial device for fitting within a cellular phone handset.

Referring to FIG. 4, a schematic view is shown of such a remedial device, comprising a coil 2 pressed into the surface of a handset battery 3, coupled to a unitary component 4, which incorporates the RF sensing antenna, and the electronics of the remedial device. The unit 4 may be coupled to the handset battery for power; alternatively it may incorporate its own power source.

Figure 5:
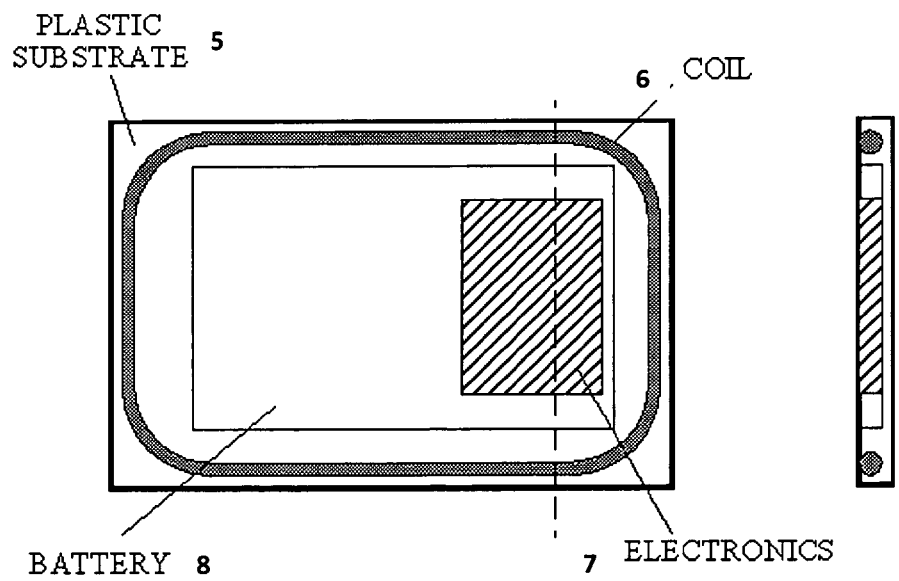
FIG. 5 is a plan view and sectional view of a remedial device, of credit card dimensions, for placing adjacent a cellular phone handset.

An alternative embodiment of the remedial device is shown in FIG. 5, in the form of an article resembling a credit card, and adapted to be positioned adjacent the cell phone, for example by placing the article in a holder or jacket for the cell phone. The article comprises a plastic substrate 5, with a coil 6 disposed around the periphery of the substrate, and incorporating a unitary component 7 which contains the electronics of the device and an antenna for sensing RF transmissions. A battery 8 provides a source of power.

Although the invention is applicable to any cellular phone, use with cellular phones that employ the GSM protocol are particularly beneficial. This is the case because RF signals whose amplitude oscillates regularly with oscillation frequencies in the extremely low frequency (ELF) have been shown to be more likely to induce a measurable biological response than unmodulated RF signals. GSM signals are transmitted as pulse bursts with pulse width of 0.577 ms and pulse repetition rate of 4.615 ms, or equivalently, frequency of 217 Hz. Therefore these signals are likely to cause biological effects.

This embodiment discloses a device that generates an ELF noise magnetic field when a cellular telephone is transmitting RF signals that are likely to produce biological effects. Typically this is the case during voice transmissions. It is distinct from prior art in that it senses the presence of the RF signals by a non-contact means that does not require interfacing directly with the phone. It is also distinct from prior art in that it includes means for activation of the remedial signal that incorporates specific features that account for certain response characteristics of biological cells to EMF stimuli. In the typical application the device described in this embodiment is located in close proximity to the phone, for instance within the battery pack that provides power to the phone. The device operates continuously with very low power consumption which increases when the remedial signal needs to be turned on.

FIG. 1 shows a general block diagram representation of the principal components of this preferred embodiment. Four principal modules are identified in this figure: RF Signal Detection Module 20, Power Control Module 22, a source of Power 24, Remedial Signal Control Module 26, and Remedial Signal Generator Module 28.

The RF Signal Detection and Analysis Module 20 includes an Antenna 30, which is coupled directly to a Passive RF Detector 32, and coupled directly an Active RF Detector 34. The Antenna may be tuned to operate at any of the common cellular phone frequencies including, for instance, 890-960, 1710-1880 MHz (GSM/DCS), and 825-894, 1820-1990 MHz (CDMA/PCS), or may be a wide band antenna that can operate within the cellular frequency range (~800 to 2000 MHz). It may be implemented as a commercial off-the-shelf chip antenna such as the MD1506, or a custom-made PCB antenna. The Passive RF Detector 32 serves the function of continuously monitoring the RF emissions from the phone and providing a control signal to actuate other components that consume more power. It is further represented in FIG. 2. In the preferred embodiment the Passive RF Detector requires no external power, relying on the strength of the received signal from antenna 20, and additionally a signal 86 from a coil 84, as will be described.

Figure 2:
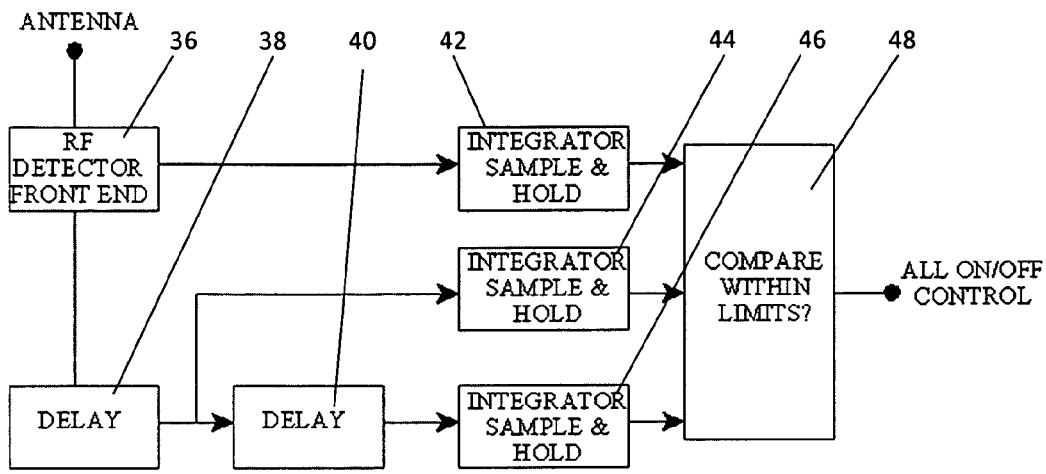
FIG. 2 is a more detailed block diagram of the passive RF detection stage of the embodiment of FIG. 1.

With reference to FIG. 2, the Passive RF Detector Front End 36 may be implemented using either a single or dual diode detector. The dual diode detector configuration which provides full wave rectification is preferred as it can also be used to provide power for the other components of the passive RF detector. This approach is often employed to actuate passive RFID devices. For instance, the HSMS-2822 or HSMS-286C Schottky diode pairs connected in series may be used for this purpose. The passive RF detector should preferably be configured to detect only voice RF transmissions. However, it may also detect other RF signals. Therefore, a comparison on successive measurements is necessary to ensure that a voice RF signal has been detected. This may be implemented, for instance, by sampling the RF front end output three times such that each sample is delayed from the next by a delay time t and then comparing the three samples. If the three samples come within a set threshold of each other, the RF signal is determined to be a likely voice RF signal. Sampling should be accomplished by integrating the signal over a time interval Ti, preferably between 50 ms and 100 ms, with successive samples delayed by the same time Ti. This is implemented as shown in FIG. 2 by first and second delay elements 38, 40, and first, second and third integrator sample and hold circuits 42, 44, and 46, which are coupled to a comparator or thresholding unit 48. Circuit 42 is coupled directly to the front end 36, circuit 44 is coupled to front end 36 via first delay unit 38, and circuit 46 is coupled to front end 36 via first delay unit 38 and second delay unit 40. Unit 48 of the passive RF signal detector produces one of the three ON/OFF control signals (All ON/OFF Control P) for the power control module, to switch on the power unit 24.

Power unit 24 provides power via power control module 22 to Active RF detector 34. Detector 34 is coupled directly to antenna 30. The Active RF Detector 34 is powered up when a talk mode signal is detected. This detector is intended to make more accurate and stable measurements of the talk mode signal. It may be implemented using commercial off-the-shelf components. As with the Passive RF Detector, sampling should be accomplished by integrating the signal over a time interval Tia, preferably of the order of 50 ms. Two successive measurements should be averaged and compared against a fixed threshold value to generate an ON or OFF signal. The output of the Active RF Detector is a train of ON/OFF values that are updated in successive 100 ms intervals. The functionality of the Active RF Detector may also be implemented using the passive RF detector. However this option would require careful adjustment to minimize false positive voice transmission detection. The output of Active RF Detector 34 is applied to remedial signal control module 26. Module 26 receives power via power control module 22 from power source 24 in response to the control signal from passive RF detector 32.

The Power Control Module 22 includes three power controls signals, one from the Passive RF Detector for all active components (All ON/OFF Control P) 50, and two from the Remedial Signal Control Module 26, one for the Active RF Detector 34 (Active ON/OFF Control) 52 and one for all active components (All ON/OFF Control A) 54. Signals 52, 54 are applied through an OR gate 56 to power source 24, so that if either of the signals for all active components is ON, the power control module 22 provides a signal to actuate all components that are powered by a power source. The Remedial Signal Control Module 26 provides an enabling/disabling signal (Active ON/OFF Control) 52 via a disabling circuit 58 for reduced power consumption of the Active RF Detector 34 as described below. In the preferred embodiment the power source is the cell phone battery cell but another power source, for instance, an auxiliary battery, could also be used.

Figure 3:
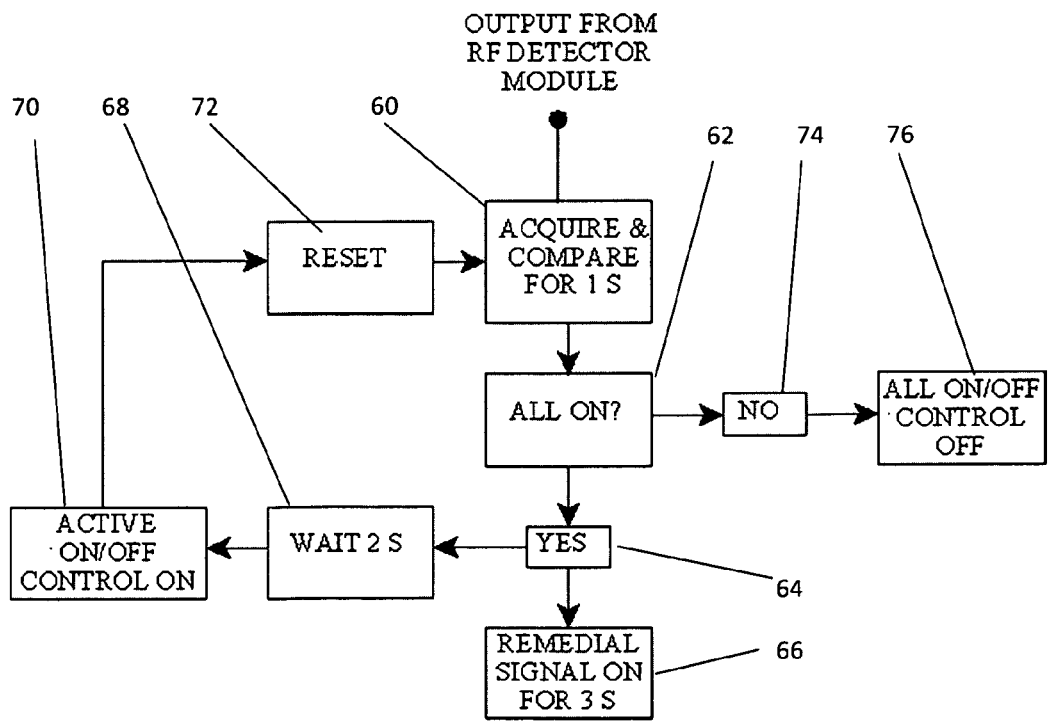
FIG. 3 is a flow chart, illustrating the method of operation of the remedial signal generator and control module of FIG. 1.

The Remedial Signal Control Module 26 incorporates the rules to control the activation of the remedial signal based on the input from the RF Detection Module 20. This module may be implemented in hardware but is most easily implemented in software using, for instance, a microcontroller. FIG. 3 shows a block diagram of a flow chart of operation for the Remedial Signal Control Module. The Acquire and Compare block 60 synchronizes with the output of the RF Detection Module and reads the values of successive samples spaced at 100 ms intervals. Reading is carried out over a time interval greater than 1 s, but preferably of the order of 1 s. If all the values are ON as at 62, a signal is applied to the remedial signal generator module 28 so that the remedial signal is turned ON, as at 64, 66 for a time interval Tp, preferably of the order of 3 s. A shorter time (>100 ms) would require more frequent detection of the RF signal. A longer time may increase the power consumption to an unacceptable level. For the first 2 s (or Tp−1 s for Tp>1 s) that the remedial signal is ON, the power control signal for the active RF detector is set to OFF to reduce power consumption (Active ON/OFF Control OFF). At the end of this 2 second interval as at 68, 70, 72, the Acquire and Compare block is Reset and the check cycle to determine whether the status of remedial signal is repeated. If any of the values measured in the compare and control block is OFF, the power control signal for all active components is set to OFF (All ON/OFF Control Off) as at 74, 76 and the device reverts to monitoring the RF signal from the phone in passive mode.

The Remedial Signal Generator Module 28 may be implemented as electromagnetic noise using an analog circuit or a mixed analog/digital circuit as previously described in U.S. Pat. No. 5,544,665 and related patents. For the purpose of this application, the preferred embodiment would employ a mixed analog/digital approach using a microcontroller for the digital section. This is advantageous because a preferred embodiment of the remedial signal control module also uses a microcontroller that could be employed to accomplish both functions. In a preferred embodiment the digital noise generator 80 can be implemented as a pseudo random noise generator consisting of appropriately interconnected shift register sequence to which an input clock signal is applied. The output bits and clock frequency are then selected to achieve the desired sequence repetition rate. For instance, with a clock rate of 4 KHz and an 18 stage shift register sequence, a repetition period of about 1 minute can be obtained. Using a digital to analog converter (DAC) and an appropriately selected band pass filter 82 a suitable noise signal can be obtained. For instance a 3-bit DAC and a 30-90 Hz band pass filter produce a noise remedial signal that satisfies the specifications of U.S. Pat. No. 5,544,665. An audio signal amplifier of standard design and a coil 84 of suitable dimensions can be used to complete the remedial signal generator. In a preferred embodiment, the coil should be a multi-turn coil with more than 100 turns and having resistance of less than 30 Ohms. For instance, AWG 36 or AWG37 copper wire can used to satisfy the coil resistance and number of turns requirements.

In this embodiment, the coil 84 is configured to sense the RF transmissions from the handset, and to provide a signal on line 86 to passive RF detector 32, in order to amplify the strength of the sensed signal input to detector 32. Such an arrangement requires that the sensed transmissions signal and the remedial noise signal can be effectively isolated. To avoid such isolation requirements, a modification of the embodiment of FIG. 1 is shown in FIG. 6.

Figure 6:
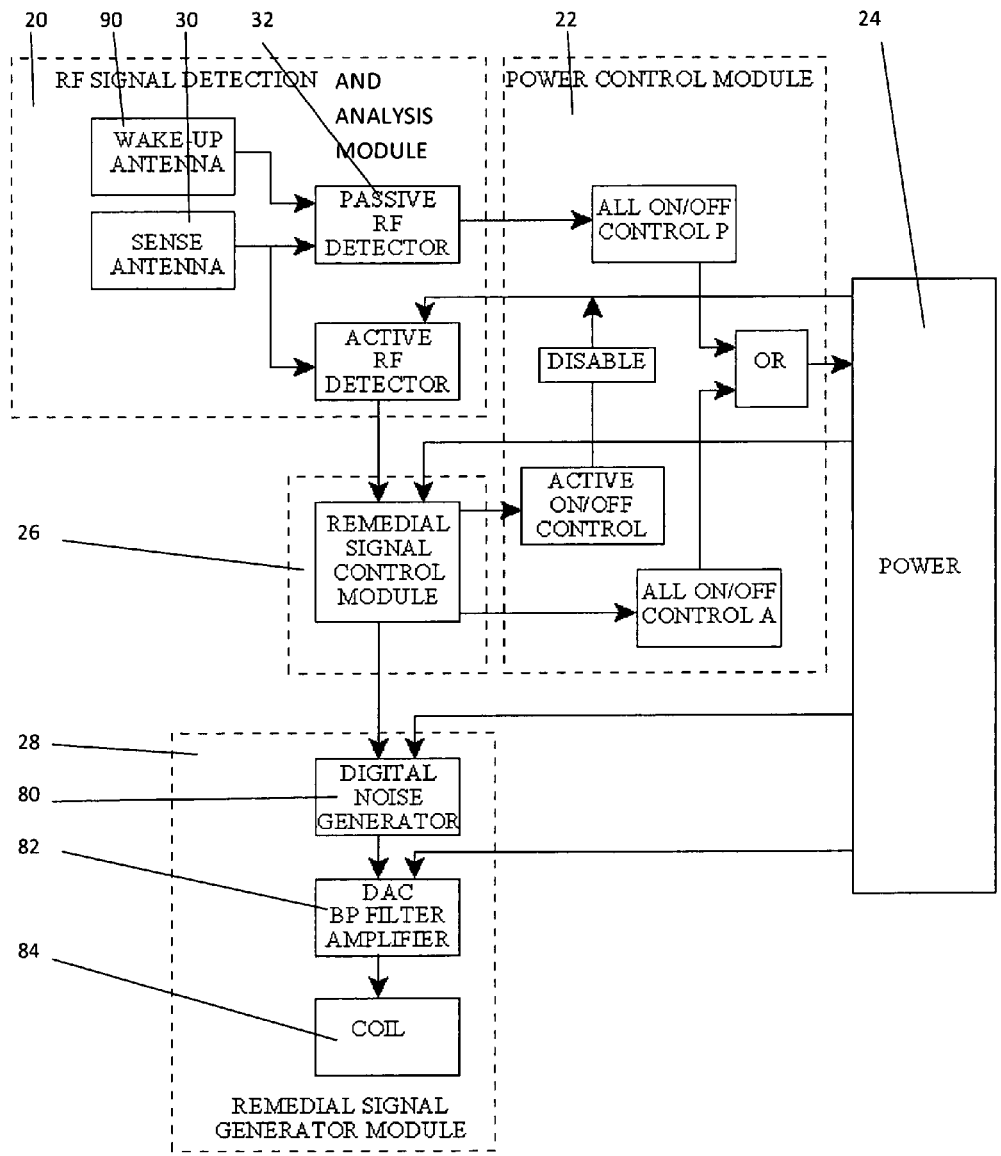
FIG. 6 is a schematic block diagram, similar to FIG. 1, of a modification of the embodiment of FIG. 1.

In FIG. 6, similar parts to those of FIG. 1 are denoted by the same reference numeral. An additional coil 90, termed a wake-up antenna, comprises a physical coil of wire or a coil traced on the PCB of the electronics of the embodiment. The effect of coil 90 is to amplify the strength of the sensed signal input to detector 32.

In a further modification of the embodiment of FIG. 1, the connecting line 86 between coil 84 and passive RF detector 32 is omitted, so that the detector 32 relies solely on the strength of the signal from antenna 30.

Figure 7:
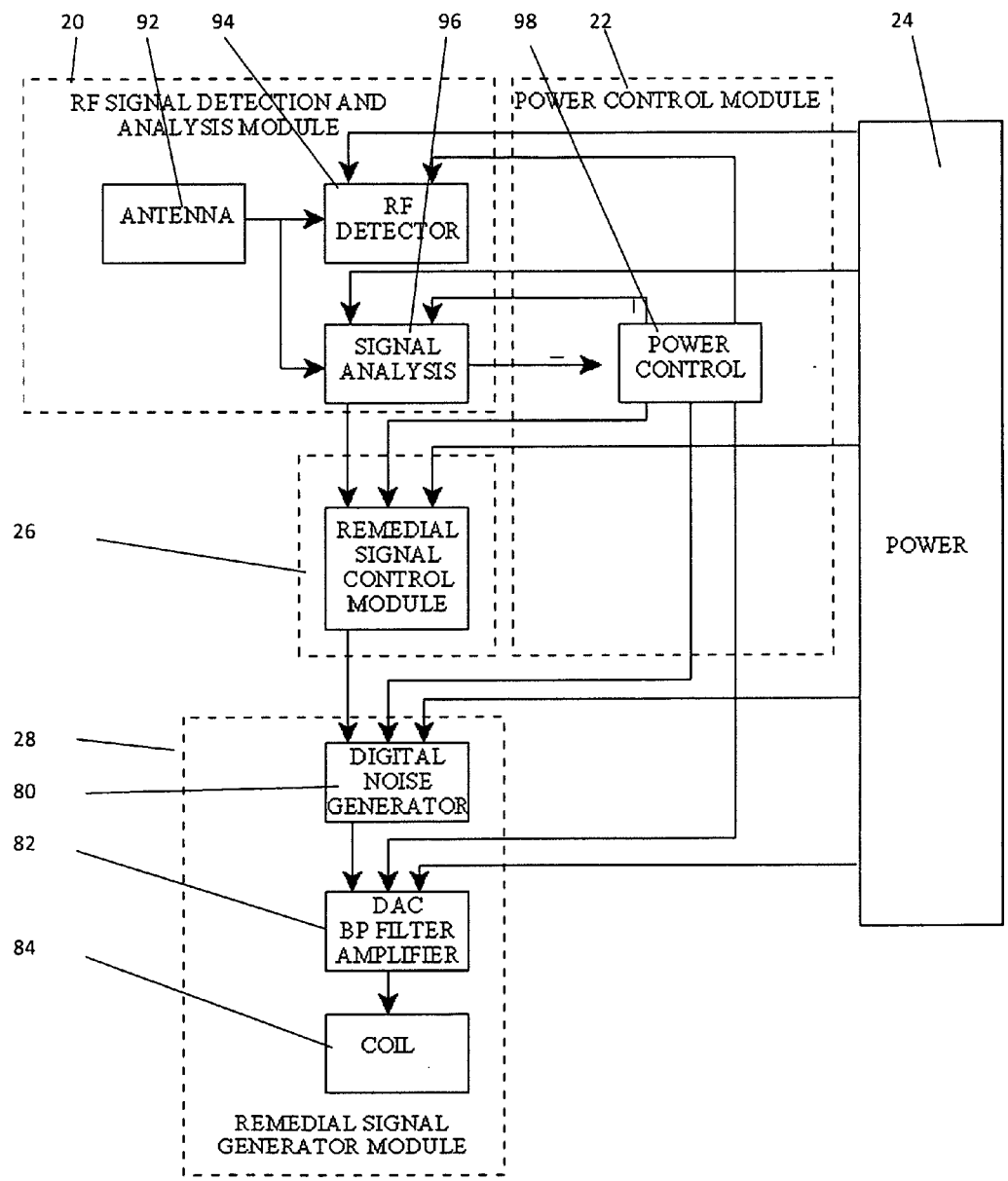
FIG. 7 is a schematic block diagram of a modification of the embodiment of FIG. 1 which does not employ the passive detection module.

In FIG. 7, similar parts to those of FIG. 1 are denoted by the same reference numeral. The passive detector module and power control via this module have been eliminated, since it was determined that the power drain could be maintained at an acceptable level even without using the passive RF detector module; therefore, the passive RF detector module is not used. Instead, the device is always ON in sleep mode (low power drain) and it is periodically awakened (1 second intervals) to determine if an RF signal is present. The RF Signal Detection and Analysis Module is composed of an antenna 92 and RF detector 94 and a signal analysis module 96 that incorporates similar functions as those of the implementations of FIGS. 1 and 6 RF detector 94 is operative to detect RF transmission signals that may be of a type that may contain harmful radiation, and is operative to actuate signal analysis module 96 In this case, the signal analysis or processing module 96 is more easily implemented using a microprocessor loaded with a software program that identifies whether a signal sensed by the antenna is a voice or data transmission and the type of the transmission protocol. Based on this information the software determines whether the protection signal needs to be activated and the magnitude of the protection signal. Hence module 96 provides an actuation signal to power control unit 98, which is operative to switch on power to remedial signal control module 26 and generator module 28.

The invention claimed is:

1. A remedial device for association with a cellular telecommunications handset that receives and transmits voice transmission, text messages e-mails and computer data and that emits RF transmissions potentially harmful to humans or animal life, the remedial device including a detection means and a remedial signal generator means, the detection means including an antenna for sensing a presence of said RF transmissions emitted by said cellular telecommunications handset, and also including a means for analyzing the RF transmissions to distinguish between voice and non-voice communication to determine their ability to produce biological effects, said detection means being coupled for actuation of said remedial signal generator means, and the remedial signal generation means being arranged to establish a remedial electromagnetic field in vicinity of the cellular telecommunications handset;
wherein said remedial device is located within the cellular telecommunications handset; and
wherein said remedial device comprises a unitary component located adjacent to a battery of the cellular telecommunications handset, said unitary component including said antenna, said detection means, and said remedial signal generation means.

2. The remedial device according to claim 1, including a coil for establishing said remedial electromagnetic field, located adjacent said battery and being connected to said remedial signal generation means.

3. The remedial device according to claim 1, wherein said remedial device is adapted to be placed adjacent the cellular telecommunications handset.

4. The remedial device according to claim 3, wherein said remedial device is in the form of a two-dimensional card.

5. The remedial device according to claim 4, wherein said antenna comprises or includes a coil which is configured to sense the RF transmissions emitted by said cellular telecommunications handset.

6. The remedial device according to claim 1, including a means for establishing a remedial field in the vicinity of the remedial device comprising a coil for establishing the remedial electromagnetic field.

7. A remedial device for association with for a cellular telecommunications handset that receives and transmits voice transmission, text messages e-mails and computer data and that emits RF transmissions potentially harmful to humans or animal life, the remedial device including a detection means and a remedial signal generator means, the detection means including an antenna for sensing a presence of said RF transmissions emitted by said cellular telecommunications handset, and also including a means for analyzing the RF transmissions to distinguish between voice and non-voice communication to determine their ability to produce biological effects, said detection means being coupled for actuation of said remedial signal generator means, and the remedial signal generation means being arranged to establish a remedial electromagnetic field in a vicinity of the cellular telecommunications handset; and
wherein said detection means comprises a detection stage including a first integration means for integrating a detected transmission signal over a predetermined time interval, a time delay means for feeding the detected transmission signal to, a second integration means for integrating the detected transmission signal over said predetermined time interval, and a means for comparing the integrated values from said first and second integration means in a threshold or comparison means in order to determine whether said RF transmissions have a significant time duration.

8. The remedial device according to claim 7 wherein said detection stage comprises a passive detection stage, having a front end which rectifies the detected transmission signal in order to derive power for operation, and which is arranged continuously to monitor the RF transmissions.

9. The remedial device according to claim 8 wherein said passive detection stage, in response to a positive determination that said RF transmissions have a significant time duration, is arranged to initiate a power on signal for switching power on in an active detection stage of the detection means, wherein the active detection stage is coupled to receive said detected transmission signal and includes a first integration means for integrating a detected transmission signal over a predetermined time interval, a time delay means for feeding the detected transmission signal to a second integration means for integrating the detected transmission signal over said predetermined time interval, and means for comparing the integrated values from said first and second integration means in a threshold or comparison means in order to determine whether said RF transmissions have a significant time duration, and to activate in response to a positive determination, said remedial signal generation means.

10. The remedial device according to claim 8, wherein said detection stage has a second time delay means coupled to the time delay means for feeding the detected transmission signal to a third integration means for integrating the detected transmission signal over said predetermined time interval, and means for comparing the integrated values from said first, second and third integration means in said threshold or comparison means.

11. The remedial device according to claim 8, wherein said significant time duration is about 100 milliseconds.

12. A remedial device for association with a cellular telecommunications handset that receives and transmits voice transmission, text messages e-mails and computer data and that emits RF transmissions potentially harmful to humans or animal life, the remedial device including a detection means and a remedial signal generator means, the detection means including an antenna for sensing a presence of said RF transmissions emitted by said cellular telecommunications handset, and also including a means for analyzing the RF transmissions to distinguish between voice and non-voice communication to determine their ability to produce biological effects, said detection means being coupled for actuation of said remedial signal generator means, and the remedial signal generation means being arranged to establish a remedial electromagnetic field in a vicinity of the cellular telecommunications handset; and
wherein said remedial signal generator means includes a remedial signal control means responsive to said detection means, a remedial signal generator, and a means for establishing a remedial field in a vicinity of the remedial device, wherein the remedial signal control means includes a monitor means to monitor an output from the detection means for a first predetermined time period sufficiently long to indicate that radiation from the cellular telecommunications handset may be potentially harmful, following which the remedial signal control means is arranged to provide power to the remedial signal generator to establish the remedial field for a second predetermined time period.

13. The remedial device according to claim 12, wherein the remedial signal control means, once activated, is arranged to disable, at least partly, the means for analyzing to reduce power drain.

14. The remedial device according to claim 12, wherein at an end of the first predetermined time period, the remedial signal control means is arranged to reset said monitor means, and awaits further outputs from the means for analyzing.

15. The remedial device according to claim 12, wherein said remedial signal generation means includes a digital noise generator, which is coupled through digital to analog conversion means and filter means, for providing an analog form of the remedial field.

16. The remedial device according to claim 12, wherein said remedial signal control means and/ or said remedial signal generator comprises a microcontroller encoded with algorithms to perform functions of said remedial signal control means and/or said remedial signal generator.

17. The remedial device according to claim 12, including a power control means for controlling a source of power, and wherein said detection means is arranged to provide an enabling signal to the power control means for supply of power to said remedial signal generation means.

18. The remedial device according to claim 17, wherein the remedial signal control means is arranged to provide an enabling signal to the power control means for supply of power to said remedial signal generator.

* * * * *

UNITED STATES PATENT AND TRADEMARK OFFICE
CERTIFICATE OF CORRECTION

PATENT NO.         : 9,571,146 B2
APPLICATION NO.    : 14/823498
DATED              : February 14, 2017
INVENTOR(S)        : Luis Miguel Penafiel It is certified that error appears in the above-identified patent and that said Letters Patent is hereby corrected as shown below:

In the Claims

Column 10, Line 43, insert --,-- after "text messages"
Column 10, Line 55, insert --a-- after "field in"
Column 11, Line 14, delete "for" after "association with"
Column 11, Line 17, insert --,-- after "text messages"
Column 11, Line 34, delete "," after "signal to"
Column 12, Line 11, insert --,-- after "text messages"

Signed and Sealed this
Sixteenth Day of May, 2017

Michelle K. Lee
*Director of the United States Patent and Trademark Office*